US006243897B1

(12) United States Patent
Sumiya

(10) Patent No.: US 6,243,897 B1
(45) Date of Patent: Jun. 12, 2001

(54) THERAPEUTIC BED FOR INVERSELY SUSPENDING/STANDING HUMAN BODY

(76) Inventor: Kozo Sumiya, 1-7 Oshima 6-chome Koto-ku, Tokyo, 136-0072 (JP)

( * ) Notice: Subject to any disclaimer, the term of this patent is extended or adjusted under 35 U.S.C. 154(b) by 0 days.

(21) Appl. No.: 09/580,040

(22) Filed: May 26, 2000

Related U.S. Application Data

(63) Continuation-in-part of application No. 09/462,982, filed as application No. PCT/JP98/02420 on Jun. 2, 1998, now abandoned.

(30) Foreign Application Priority Data

| | | |
|---|---|---|
| Jul. 22, 1997 | (JP) | 9-7495 |
| Sep. 16, 1997 | (JP) | 9-9340 |

(51) Int. Cl.$^{7}$ .......... A61G 7/005; A61G 7/015; A61H 1/02; A61F 5/045

(52) U.S. Cl. .......... 5/610; 5/618; 5/621; 5/624; 482/144

(58) Field of Search .......... 5/610, 608, 600, 5/618, 613, 621, 624; 482/143, 144, 145; 601/5, 24

(56) References Cited

U.S. PATENT DOCUMENTS

| | | | | |
|---|---|---|---|---|
| 2,887,691 | * | 5/1959 | Talarico et al. | 5/610 |
| 3,149,349 | * | 9/1964 | Nelson | 5/610 |
| 3,286,708 | * | 11/1966 | Gärtner | 482/144 |
| 3,388,700 | * | 6/1968 | Mountz | 482/144 |
| 4,557,471 | * | 12/1985 | Pazzini | 5/610 |
| 4,672,697 | * | 6/1987 | Schürch | 482/144 |
| 5,967,956 | * | 10/1999 | Teeter | 482/144 |

FOREIGN PATENT DOCUMENTS

| | | |
|---|---|---|
| 54-909990 | 6/1979 | (JP) . |
| 56-116029 | 9/1981 | (JP) . |
| 1-178012 | 12/1989 | (JP) . |
| 6-47068 | 12/1994 | (JP) . |

* cited by examiner

*Primary Examiner*—Alexander Grosz
(74) *Attorney, Agent, or Firm*—Muramatsu & Associates

(57) ABSTRACT

An automatic therapeutic bed for inversely suspending/standing a human body includes an intermediate member of the therapeutic bed, a backrest of the therapeutic bed rotatably connected to an end of the intermediate member for accommodating an upper body of the patient, a footrest of the therapeutic bed rotatably connected to another end of the intermediate member for accommodating a lower body of the patient, a plurality of frames provided under the intermediate member, the backrest and the footrest and forming a bed angle adjustment mechanism, a drive means for driving the bed angle adjustment mechanism formed of the frames to change the angles and positions of the intermediate member, the backrest and the footrest of the therapeutic bed, shoulder pads provided at an end of the backrest for supporting shoulders of the patient, and a fastening means provided at an end of the footrest for fastening ankles of the patient.

15 Claims, 7 Drawing Sheets

THERAPEUTIC BED FOR INVERSELY SUSPENDING/STANDING HUMAN BODY

This is a continuation-in-part of U.S. patent application Ser. No. 09/462,982 filed Jan. 14, 2000 now abandoned, which is a 371 of PCT/JP98/02420, filed Jun. 2, 1998.

FIELD OF THE INVENTION

The present invention is related to a therapeutic bed for chiropractic or medical treatment of a human body, or protecting a human body from disease by inversely suspending/standing the human body while holding the human body on the bed not to fall down.

BACKGROUND OF THE INVENTION

The backbone of a human body is formed of a large number of cylindrically shaped vertebrae where each vertebra is connected to the adjacent vertebra by a disc of cartilage. Hernia may be caused when the disc cartilages are slipped and compressed or injured, resulting in severe back ache and requiring chiropractic or other treatment as well as rehabilitation. To be used in such a situation, in the past, therapeutic tools are known such as health hanging tools for home use and expanding machines for hospital use. Such therapeutic tools, however, are difficult to use for a long period of time or difficult to operate for a person who has diminished physical strength, or who are in poor health or confined to bed.

For such conventional tools, an improvement has been proposed where a motor is employed therein to easily operate the tool. For example, Japanese Patent Laid-Open Publication No. 6-182000 shows a therapeutic tool for inversely hanging and suspending a human body by a winch. However, such a conventional tool is disadvantageous in that only the inverse suspension mode is available, while it is relatively large and expensive.

SUMMARY OF THE INVENTION

Therefore, it is an object of the present invention to provide a therapeutic bed which is capable of overcoming the drawbacks in the conventional therapeutic tools, thereby inversely hanging or standing a human body with the maximum angle for expanding the human body.

It is another object of the present invention to provide a therapeutic bed for stretching abdominal muscles and back muscles while the therapeutic bed is in the substantially horizontal direction by up/down moving a backrest of the therapeutic bed and stretching knees by up/down moving a footrest of the therapeutic bed.

It is a further object of the present invention to provide a therapeutic bed for recovering flexibility in intervertebral discs that have been compressed and forming a healthy body, and easily achieving an inverse suspending or inverse standing treatment even for a weak or sick person.

For achieving such objectives, the therapeutic bed of the present invention includes an intermediate member of the therapeutic bed, a backrest of the therapeutic bed rotatably connected to an end of the intermediate member for accommodating an upper body of the patient, a footrest of the therapeutic bed rotatably connected to another end of the intermediate member for accommodating a lower body of the patient, a plurality of frames provided under the intermediate member, the backrest and the footrest and forming a bed angle adjustment mechanism, a drive means for driving the bed angle adjustment mechanism formed of the frames to change the angles and positions of the intermediate member, the backrest and the footrest of the therapeutic bed, shoulder pads provided at an end of the backrest for supporting shoulders of the patient, and a fastening means provided at an end of the footrest for fastening ankles of the patient.

In another aspect, the intermediate member and the footrest are integrally formed to establish an intermediate and lower body support, and the backrest is rotatably connected to the intermediate and lower body support. In a further aspect of the present invention, two hydraulic cylinders are provided, one is used for driving the backrest while the other is used for driving the intermediate and lower body support.

According to the therapeutic bed of the present invention, the plural members of the bed are first extended to form a flat and horizontal bed. A patient lies on the bed with the shoulders contacting the shoulder pads at one end of the bed and the ankles being fastened by the ankle fastening belt at another end of the bed. By rotating the therapeutic bed through the drive mechanism and sustaining in a desired inverse position, the patient can be inversely suspended on the bed.

Then, by controlling the hydraulic cylinder, the therapeutic bed is returned to the flat and horizontal state so that the patient can rest quietly on the bed. Further, in addition to inversely suspending the patient, the therapeutic bed of the present invention can perform various other functions as well. By rotatably moving the headrest, footrest or intermediate and lower support of the bed in an up/down direction, various health improvement actions can be achieved such as stretching and strengthening abdominal muscle and back muscle of the patient.

The therapeutic bed can be used protectively by a healthy person for improving strength of abdominal and back muscle so as to avoid suffering from back pain such as hernia. In addition, since the therapeutic bed of the present invention can be operated with use of keys or switch nearby, it is especially suitable for treatment of a weak and/or sick person or a bedridden person. The therapeutic bed of the present invention is especially effective for healing a back pain such as hernia or gastroptosis by stretching the back.

DETAILED DESCRIPTION OF THE PREFERRED EMBODIMENTS

The embodiments of the present invention will be described in detail with reference to the accompanying drawings. FIGS. 1–6 show the therapeutic bed for inversely suspending/standing a patient (hereinafter "therapeutic bed") in the first embodiment of the present invention.

Figure 1:
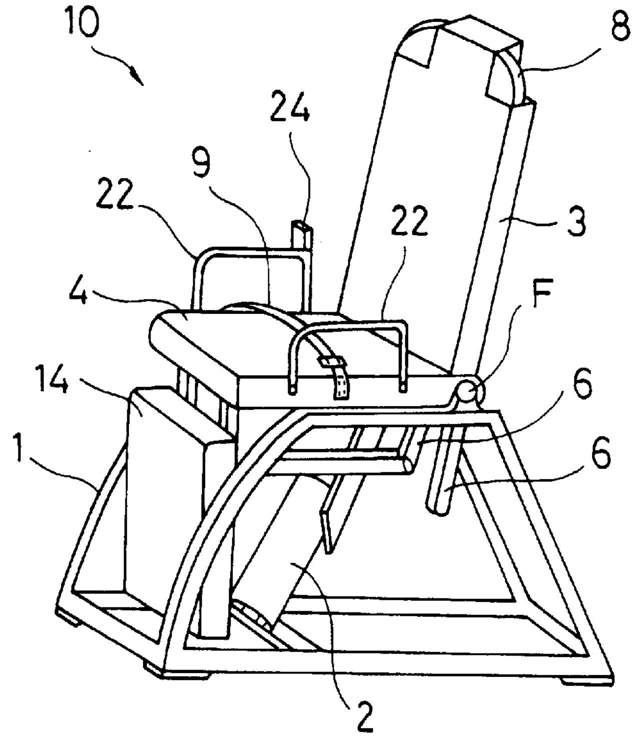
FIG. 1 is a perspective view showing a therapeutic bed 10 for inversely suspending/standing a human body in the first embodiment of the present invention.

FIG. 1 shows one of the examples of various forms available in a therapeutic bed 10 of the present invention. In the first embodiment, the therapeutic bed 10 has a support frame 1 having a trapezoidal shape. The support frame 1 is made of L-shaped light steel or high strength synthetic resin or the like, and is assembled by welding or screwing each component to form the frame to fully support the therapeutic bed and other members.

An intermediate member 4 of the therapeutic bed 10 is provided on the frame 1 in a manner rotatable about a shaft F. At one end (right side of FIG. 1) of the intermediate member 4, a backrest 3 is rotatably connected while the other end (left side of FIG. 1) of the intermediate member 4, a footrest 14 is rotatably connected. A plurality of frames 6 are respectively provided under the intermediate member 4, backrest 3 and the footrest 14.

The frames 6 are connected with one another to form a bed angle adjustment mechanism and are connected to an upper end of a hydraulic cylinder 2. The base (lower end) of the hydraulic cylinder 2 is mounted on the bottom part of the support frame 1. By extension or contraction movements of the hydraulic cylinder 2, the intermediate member 4, backrest, 3 and footrest 14 of the therapeutic bed 10 are driven via the bed angle adjustment mechanism, thereby creating various positions of the therapeutic bed 10.

Figure 3:
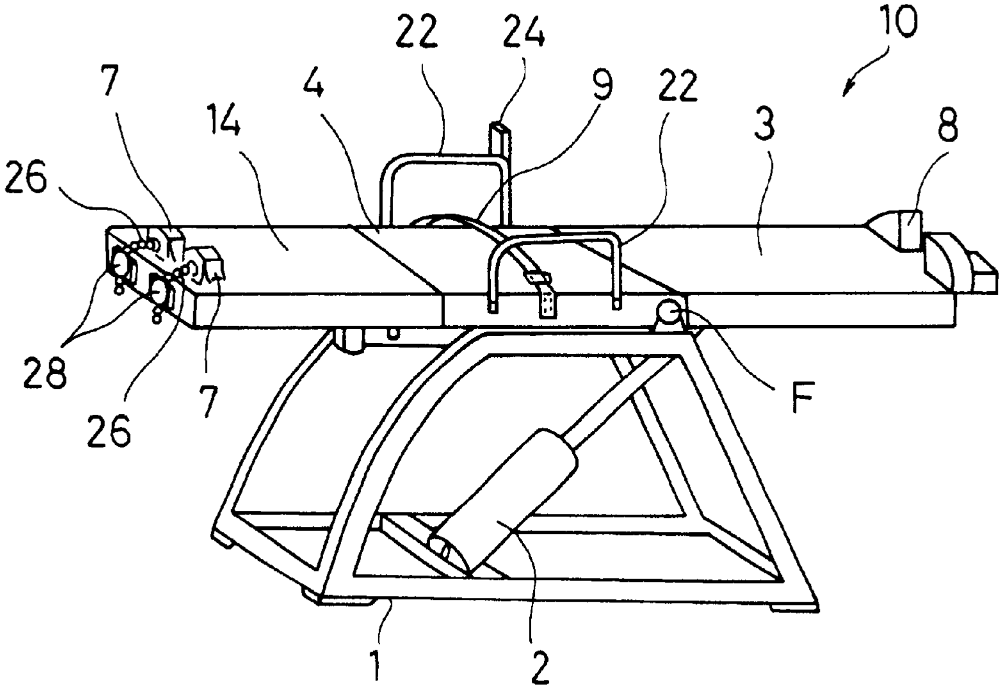
FIG. 3 is a perspective view showing the inversely suspending therapeutic bed 10 in the first embodiment in which a backrest 3, an intermediate member 4 and a footrest 14 are respectively aligned on the same horizontal surface of the bed similar to an ordinary bed.

As shown in FIGS. 1 and 3, shoulder pads 8 are provided at both sides of an upper part of the backrest 3. The shoulder pads 8 are rotatable as well as being fixed in predetermined orientations through a mechanism shown in FIG. 4. Namely, as shown in FIG. 4, a support structure 12 is provided at the top end of the backrest 3 for supporting a hook member 16.

Figure 4A:
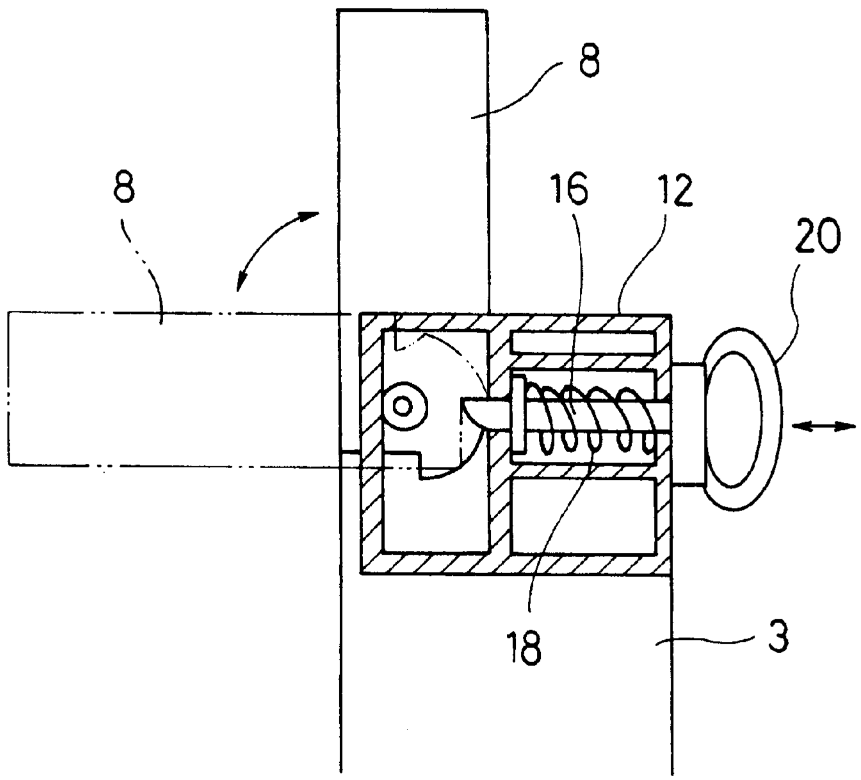
FIG. 4(*a*) is an enlarged cross sectional view showing a support structure 12 in which an end of a hook member 16 is engaged with a shoulder pad 8, and FIG. 4(*b*) is a front view of the shoulder pad 8.
Figure 4B:
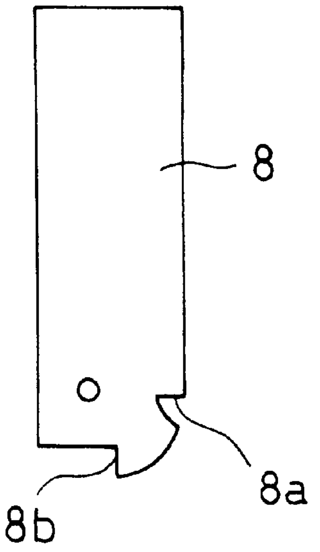

A spring 18 is provided between the support structure 12 and the hook member 16 in a manner shown in FIG. 4. When pulling a handle 20 of the hook member 16 in an outward direction, the end of the hook member 16 is disengaged from the shoulder pad 8. When releasing the handle 20, by the force of the spring 18, the end of the hook member 16 is engaged with the shoulder pad 8.

Accordingly, when the end of the hook member 16 is fitted in a first receptacle 8*a* (FIG. 4(*b*)) of the shoulder pad 8, the shoulder pad 8 is maintained in the orientation as shown by the solid line of FIG. 4(*a*). In this situation, the shoulder pads 8 are in the same flat surface of the backrest 3 and are not used as shoulder supports. When the end of the hook member 16 is fitted in a second receptacle 8*b* (FIG. 4(*b*)) of the shoulder pad 8, the shoulder pad 8 is maintained in the orientation as shown by the dotted line of FIG. 4(*a*). In this situation, the shoulder pads 8 are maintained in a direction perpendicular to the surface of the backrest 3 for supporting the patient's shoulders.

Figure 2:
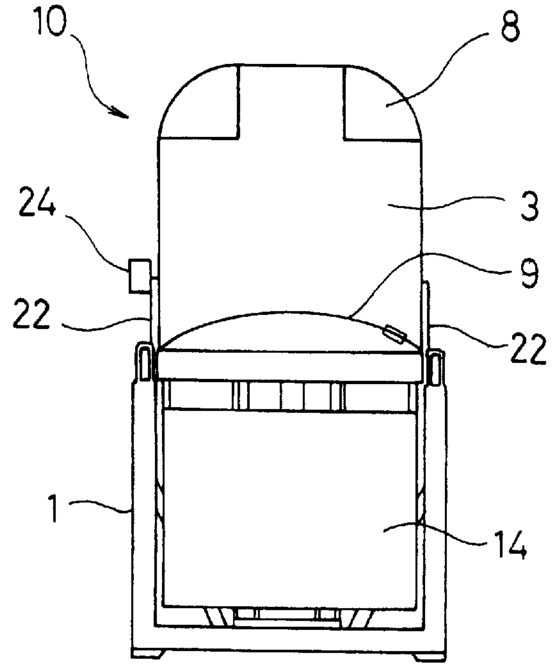
FIG. 2 is a front view showing the inversely suspending therapeutic bed 10 in the first embodiment.

As shown in FIGS. 1–3, the therapeutic bed 10 includes handrails 22 at both sides of the intermediate member 4 and a safety belt 9 connected to the both sides. A remote controller 24 is attached to one of the handrails 22 and is connected to the hydraulic cylinder 2 through a signal cable (not shown). By pressing keys on the remote controller 24, a user can control the operation of the hydraulic cylinder 2, thereby changing angles and forms of the therapeutic bed 10.

Figure 5:
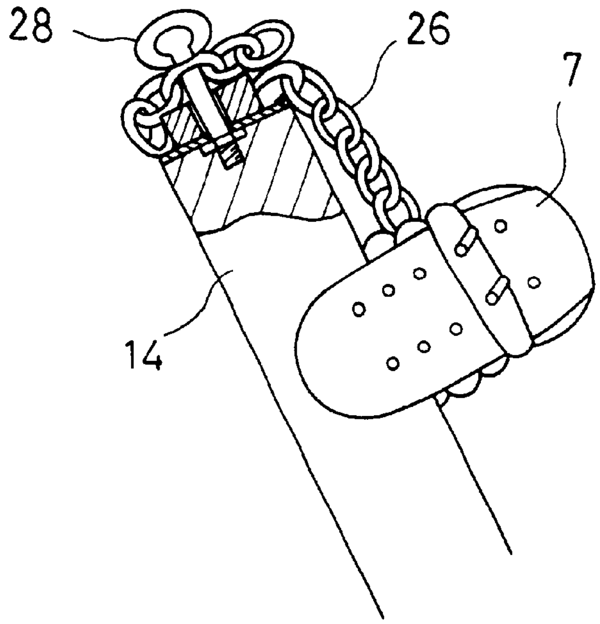
FIG. 5 is a partially cut-out enlarged side view showing an ankle fastening belt 7 and associated components in the present invention.

Further, as shown in FIG. 3, at the far end of the footrest 4, the therapeutic bed 10 includes a pair of ankle fastening belts 7. An example of ankle fastening belt 7 is shown in FIG. 5. In this example, the ankle fastening belt 7 is connected to one end of a chain 26 while the other end of the chain 26 is attached the edge of the footrest 4 through a fixture 28.

The operation of the therapeutic bed 10 of the present invention is described in the following. When the therapeutic bed 10 is in the condition as shown in FIG. 4, by manipulating the hook member 16 through the handle 20, the shoulder pads 8 are fixed on the bed with a right angle relative to the backrest 3. A patient sits on the intermediate member 4 of the therapeutic bed 10 in the same manner as sitting on a chair. The safety belt 9 on the intermediate member 4 is fastened on the patient.

With use of the remote controller 24, extraction or contraction movements of the hydraulic cylinder 2 and the associated movements of the bed angle adjustment mechanism of the frame 6 are controlled. Thus, the backrest 3, intermediate member 4, and footrest 14 of the bed 10 are extended to be in the same horizontal surface as shown in FIG. 3. The patient's ankles are fastened by the fastening belts 7, and the patient lays flat on the bed 10.

Figure 6:
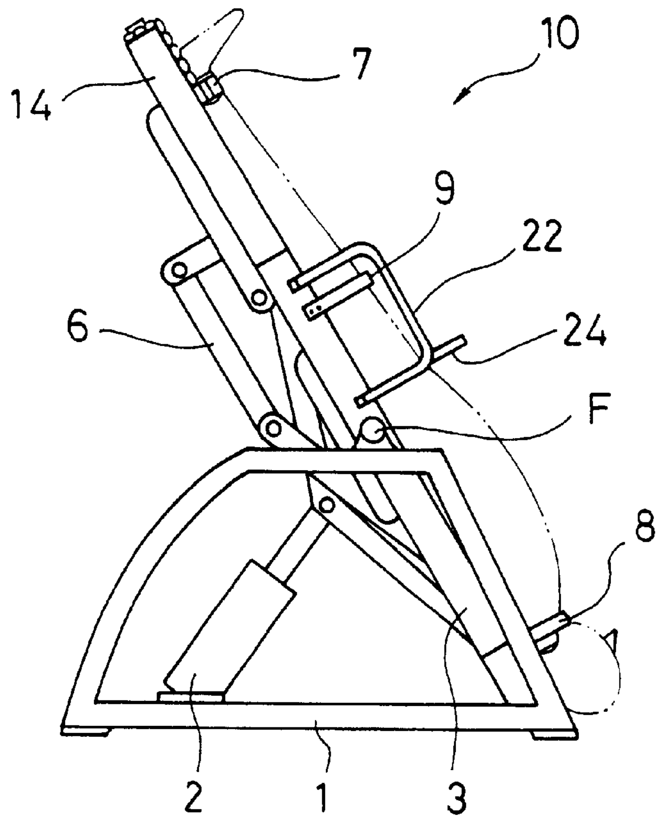
FIG. 6 is a side view showing the therapeutic bed 10 of the present invention where a patient is inversely suspended on the bed.

Then, by controlling the extraction and contraction movements of the hydraulic cylinder 2 and the frames 6 forming the bed angle adjustment mechanism, with use of the remote controller 24, the therapeutic bed 10 changes its position in the manner shown in FIG. 6. In the example of FIG. 6, the therapeutic bed 10 is inversely rotated about 80 degrees from the horizontal state so that the footrest 14 is positioned higher that the backrest 3.

In this condition, since the patient is inversely suspended on the bed in a head standing manner, a plurality of vertebrae of the patient are stretched, and the slips of the cartilages are corrected, as well as the compression of the cartilage between the vertebrae is released. As a result, the cartilages that have been compressed and/or injured because of the weight of the patient are relieved from these problems, and by the long treatment with use of the therapeutic bed of the present invention, new cartilages are reproduced, thereby completely curing the disease such as hernia.

Bloodstreams of the patient may be adversely affected if the patient is inversely suspended in the manner of FIG. 6 for a long period of time. Therefore, within an appropriate time, the patient can operate the remote controller 24 to return the therapeutic bed 10 to the original state of FIG. 3. The patient can rest quietly as long as necessary on the bed 10 which is horizontally laying as shown in FIG. 3, thereby avoiding the cartilages from immediately receiving the weight of the patient. By repeating the above noted procedures for a long time, the cartilages can be completely recovered and reproduced.

Further, weakened abdominal muscle of the patient are stretched and strengthened by repeatedly raising and falling the backrest 3 of the therapeutic bed 10. Moreover, weakened leg muscle are also stretched and strengthened by repeatedly changing the position of the footrest 4 between the horizontal position and the lower position.

Figure 7:
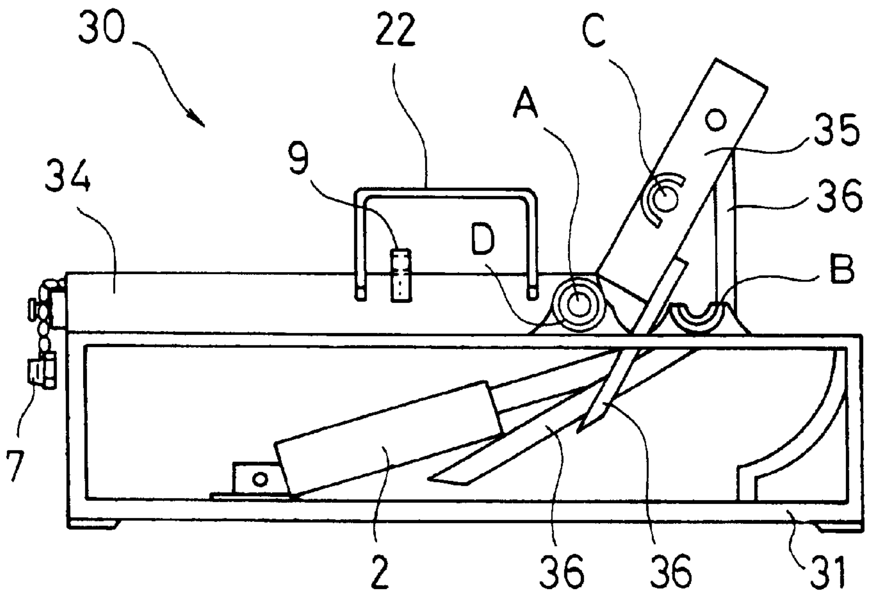
FIG. 7 is a side view showing a therapeutic bed 30 for inversely suspending/standing a human body in the second embodiment of the present invention.

FIGS. 7–11 show the therapeutic bed in the second embodiment of the present invention. FIG. 7 shows one of the examples of many variations available in a therapeutic bed 30 of the present invention. In the second embodiment, the therapeutic bed 30 has a support frame 31 having a rectangular shape. The support frame 31 is made of L-shaped light steel or high strength synthetic resin or the like, and is assembled by welding or screwing each component to form the support frame to fully support the therapeutic bed and other members.

An intermediate and lower body support 34 of the therapeutic bed 30 is provided on the frame 31 in a manner rotatable about a shaft A supported by bearing D. At one end (right side of FIG. 7) of the intermediate and lower body support 34, a backrest 35 is rotatably connected. The backrest 35 is so structured to be able to rotate about a shaft C which is supported by bearing B, as will be described later.

A plurality of frames 36 are respectively provided under the intermediate and lower body support 34 and the backrest 35. The frames 36 are connected with one another to establish a bed angle adjustment mechanism. The bed angle adjustment mechanism formed of the frames 36 is connected to an upper end of a hydraulic cylinder 2 (drive means). The base (lower end) of the hydraulic cylinder 2 is mounted on the bottom part of the support frame 31. By extension and contraction movements of the hydraulic cylinder 2, the intermediate and lower body support 34 and the backrest 35 of the therapeutic bed 30 are driven through the angle adjustment mechanism formed of the frames 36, thereby creating various positions of the therapeutic bed 30.

Figure 8:
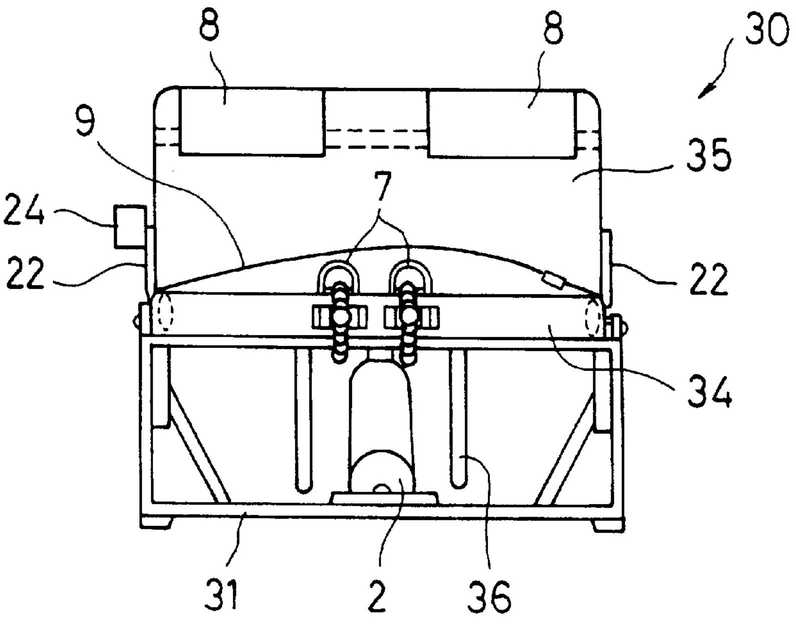
FIG. 8 is a front view of the inversely suspending therapeutic bed 30 in the second embodiment of FIG. 7.
Figure 10:
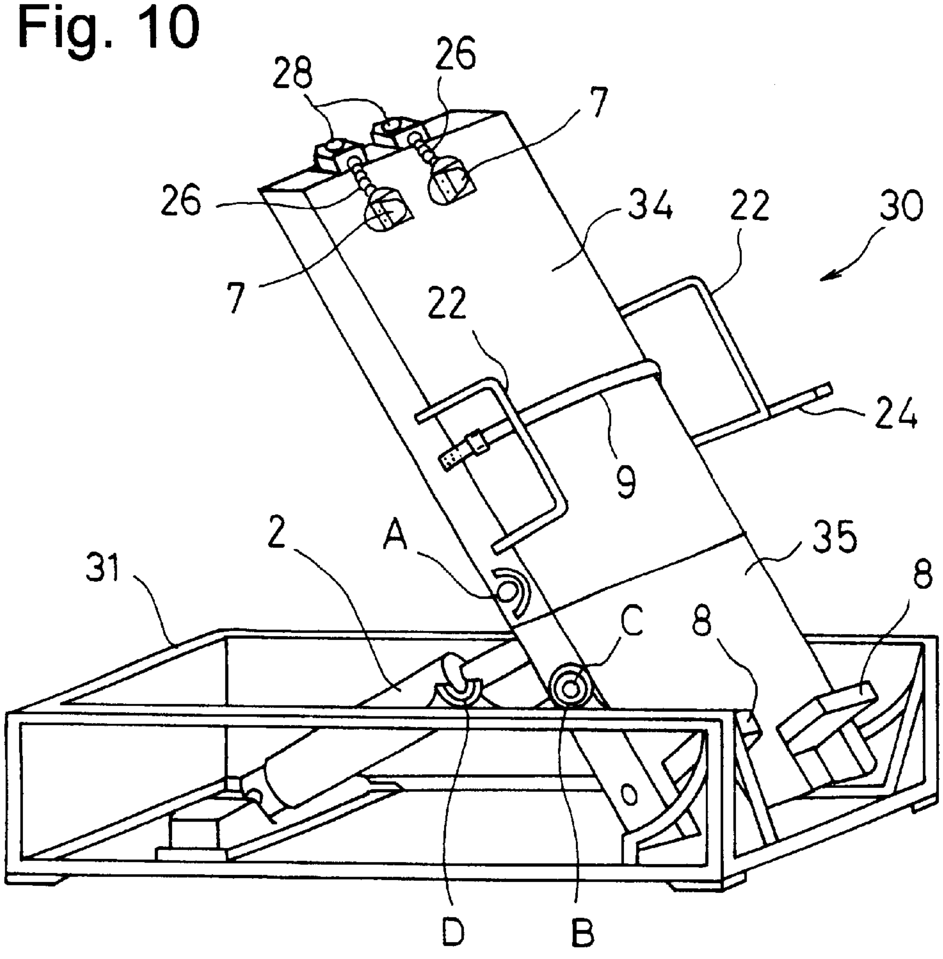
FIG. 10 is a perspective view showing the shown in the inversely suspending therapeutic bed 30 wherein a backrest 35 and an intermediate and lower body support 34 are shown in the inversed position.
Figure 9:
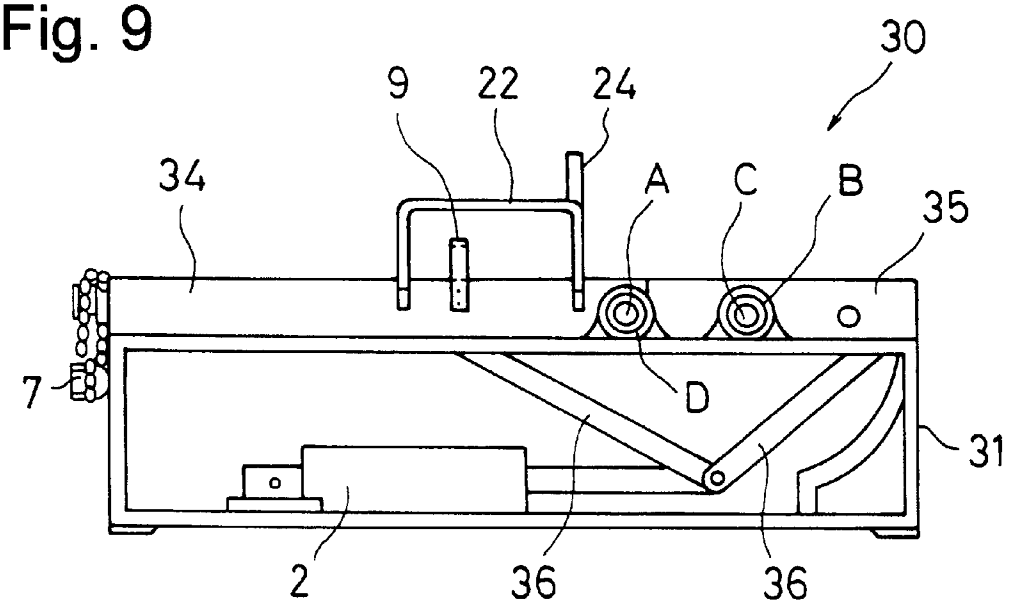
FIG. 9 is a side view showing the inversely suspending therapeutic bed 30 in the second embodiment wherein a backrest 35 and an intermediate member 34 are respectively aligned on the same horizontal surface of the bed similar to an ordinary bed.
Figure 11:
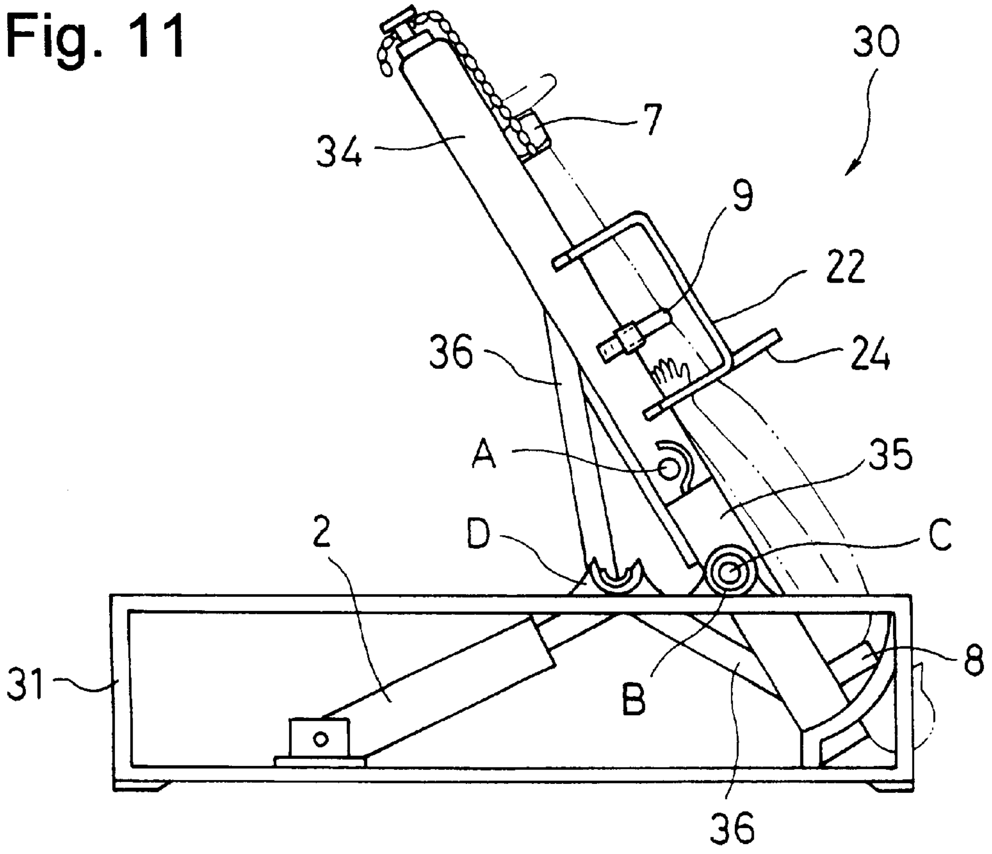
FIG. 11 is a side view showing the therapeutic bed 30 of the present invention in the inverse condition of FIG. 10 where a patient is inversely standing on the bed.

As shown in FIGS. 8 and 10, shoulder pads 8 are provided at both sides of an upper part of the backrest 35. The shoulder pads 8 are rotatable as well as being fixed in predetermined orientations by the mechanism similar to the hook member 6 and the support structure 12 described above with respect to the first embodiment. Thus, the backrest 35 is sustained in perpendicular to the backrest 35 or laid flat on the same surface of the backrest 35.

As shown in FIG. 7, the therapeutic bed 30 further includes handrails 22 at both sides of the intermediate and lower body support 34 close to the backrest 35 and a safety belt 9 connected to the both sides. A remote controller 24 is attached to one of the handrails 22 and is connected to the hydraulic cylinder 2 through a signal cable (not shown). By pressing keys on the remote controller 24, a user can control the operation of the hydraulic cylinder, thereby changing the angle and position of the therapeutic bed 10.

Further, similar to the first embodiment noted above, at the far end of the intermediate and lower body support 34 of the therapeutic bed 30, a pair of ankle fastening belts 7 are attached thereto. An example of ankle fastening belt 7 is shown in FIG. 5. The ankle fastening belt 7 is connected to one end of a chain 26 while the other end of the chain 26 is attached to the edge of the intermediate and lower body support 34 through a fixture 28.

The operation of the therapeutic bed 30 of the present invention is described in the following. When the therapeutic bed 30 is in the condition as shown in FIG. 7, the shoulder pads 8 are fixed on the bed with a right angle relative to the backrest 35 in the manner shown in FIG. 10. The waist and lower body of the patient are placed on the intermediate and lower body support 34 in FIG. 7. The safety belt 9 on the intermediate and lower body support 34 is fastened on the patient.

With use of the remote controller 24, extension and contraction movements of the hydraulic cylinder 2 and the associated movements of the bed angle adjustment mechanism are controlled. Thus, the therapeutic bed 30 changes its angle and shape in the manner shown in FIGS. 10 and 11 in which the therapeutic bed 30 is rotated and inversely sustained at an angle of about 80 degrees from the horizontal plane so that the intermediate and lower body support 34 is positioned higher that the backrest 35. As a consequence, the patient is inversely suspended in a head standing manner on the therapeutic bed 30.

Since the patient is inversely suspended on the therapeutic bed, the vertebra of the patient are stretched and the cartilage slip can be corrected as well as the compression of the cartilage between the vertebrae is released. Further, by controlling the hydraulic cylinder 2 and the frames 36, the therapeutic bed 30 can be returned to the flat and horizontal state of FIG. 9 so that the patient can rest quietly on the bed 30. Further, weakened abdominal muscle and back muscle of the patient are stretched and strengthened by repeatedly raising (FIG. 9) and falling (FIG. 7) the backrest 35 of the therapeutic bed 30.

Figure 12:
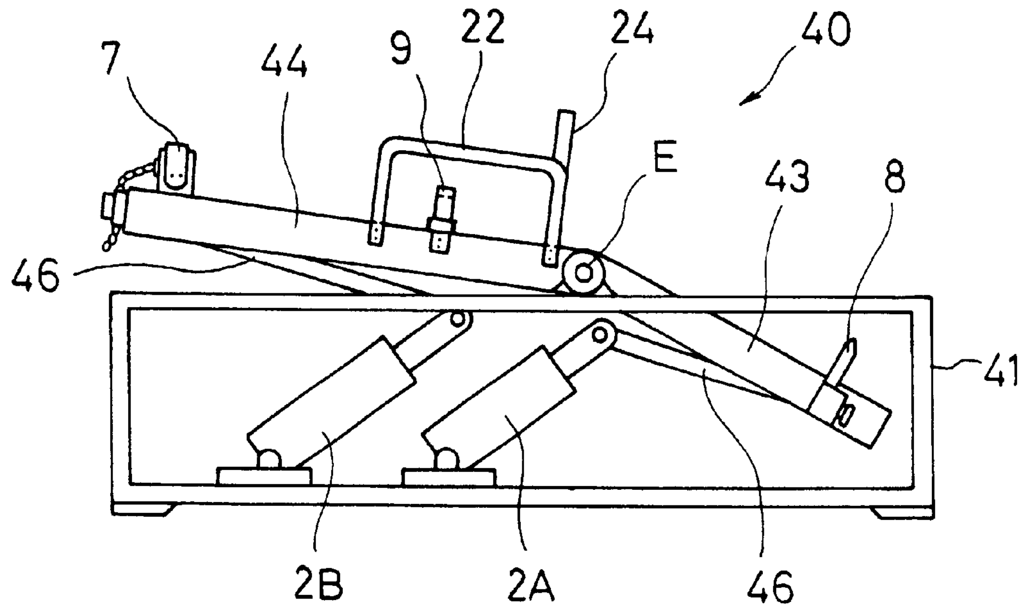
FIG. 12 is a side view showing a therapeutic bed 40 for inversely suspending/standing a human body in the third embodiment of the present invention wherein the therapeutic bed is suitably angled for stretching the abdominal muscle of the patient.
Figure 13:
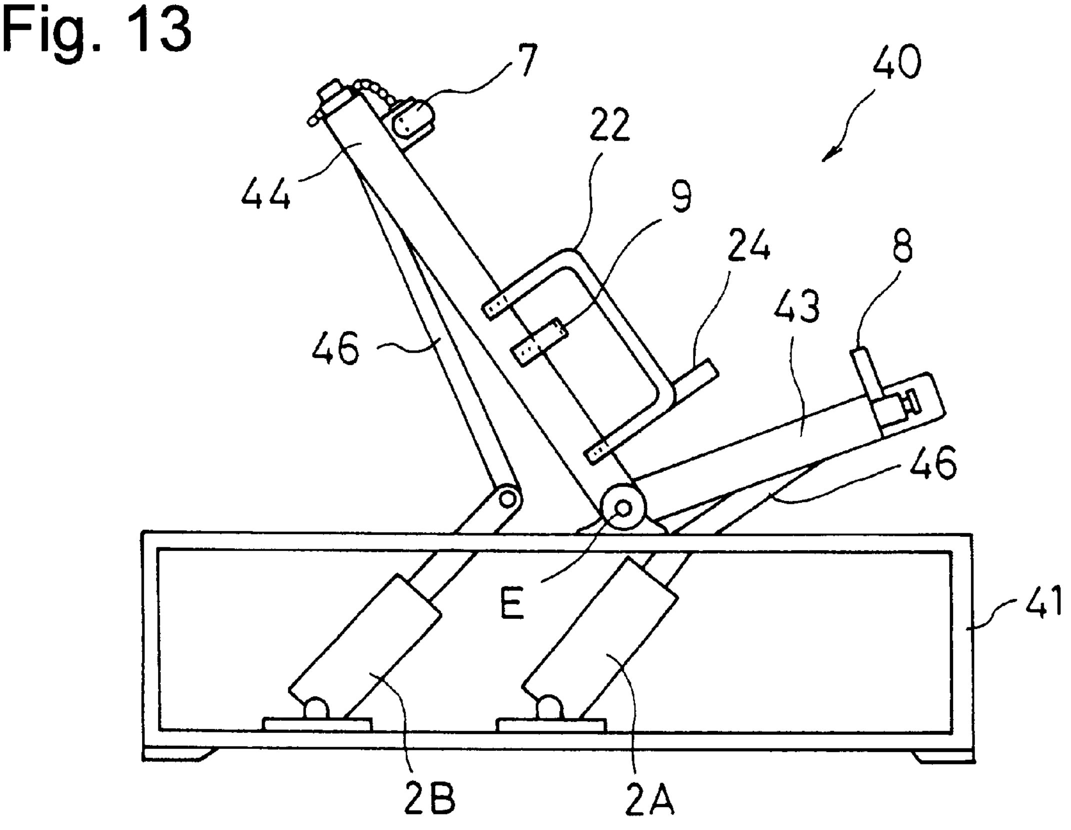
FIG. 13 is a side view of the inversely suspending therapeutic bed 40 in the third embodiment of FIG. 12 wherein the therapeutic bed is suitably angled for stretching the back muscle of the patient.

FIGS. 12 and 13 show the therapeutic bed in the third embodiment of the present invention. In the third embodiment, a therapeutic bed 40 is configured by a backrest 43 and an intermediate and lower body support 44 and is supported on a support frame 41 having a rectangular shape, which is the same as the therapeutic bed 30 in the third embodiment in the foregoing. However, the therapeutic bed 40 is different from the therapeutic bed 30 in that it has only one set of bearing E for rotatably supporting the bed 40 and two hydraulic cylinders 2A and 2B.

In the therapeutic bed 40 configured in this manner, not only the patient can be inversely suspended but various forms and angles of the bed can be made as well. Namely, with use of the remote controller 24, the hydraulic cylinders 2A and 2B are independently controlled from one another, thereby independently changing the positions and angles of the backrest 43 and intermediate and lower body support 44 through the frames 46. Therefore, the therapeutic bed 40 can treat the disease such as hernia of the patient and can stretch and strengthen the weakened muscle of the patient with further freedom and flexibility.

As described in the foregoing, the therapeutic bed of the present invention, the plural members of the bed are first extended to form a flat and horizontal bed. A patient lies on the bed with the shoulders contacting the shoulder pads at one end of the bed and the ankles being fastened by the ankle fastening belt at another end of the bed. By rotating the therapeutic bed through the drive mechanism and sustaining in a desired inverse position, the patient can be inversely suspended on the bed.

Then, by controlling the hydraulic cylinder, the therapeutic bed is returned to the flat and horizontal state so that the patient can rest quietly on the bed. Further, in addition to inversely suspending the patient, the therapeutic bed of the present invention can perform various other functions as well. By rotatably moving the headrest, footrest or intermediate and lower support of the bed in an up/down direction, various health improvement actions can be achieved such as stretching and strengthening abdominal muscle and back muscle of the patient.

The therapeutic bed can be used protectively by a healthy person for improving strength of abdominal and back, muscle so as to avoid suffering from back pain such as hernia. In addition, since the therapeutic bed of the present invention can be operated with use of keys or switch nearby, it is especially suitable for treatment of a weak and/or sick person or a bedridden person. The therapeutic bed of the present invention is especially effective for healing a back pain such as hernia or gastroptosis by stretching the back.

Although only a preferred embodiment is specifically illustrated and described herein, it will be appreciated that many modifications and variations of the present invention are possible in light of the above teachings and within the purview of the appended claims without departing the spirit and intended scope of the invention.

What is claimed is:

1. A therapeutic bed for inversely suspending/standing a patient, comprising:

an intermediate member of the therapeutic bed;

a backrest of the therapeutic bed rotatable connected to an end of the intermediate member for accommodating an upper body of the patient;

a footrest of the therapeutic bed rotatable connected to another end of the intermediate member for accommodating a lower body of the patient;

a plurality of frames provided under the intermediate member, the backrest and the footrest and forming a bed angle adjustment mechanism;

a drive means for driving the bed angle adjustment mechanism formed of the frames to change the angles and positions of the intermediate member, the backrest and the footrest of the therapeutic bed;

shoulder pads provided at an end of the backrest for supporting shoulders of the patient; and a fastening means provided at an end of the footrest for fastening ankles of the patient.

2. A therapeutic bed as defined in claim 1, further comprising handrails provided on both sides of the intermediate member for being grasped by the patient and for preventing the patient from falling down from the bed.

3. A therapeutic bed as defined in claim 2, further comprising a remote controller provided adjacent to one of the handrails to control movements of the drive means for changing the angle and position of at least one of the intermediate member, the backrest and the footrest through the bed angle adjustment mechanism.

4. A therapeutic bed as defined in claim 2, further comprising a safety belt on the intermediate member for fastening on the patient to promote safety when the therapeutic bed moves.

5. A therapeutic bed as defined in claim 1, wherein the shoulder pads on the backrest take two fixed orientations, one of which is in perpendicular to the horizontal plane of the backrest and the other is in the same direction of the horizontal plane of the backrest.

6. A therapeutic bed as defined in claim 1, wherein the shoulder pads on the backrest have two receptacles to receive a hook therein for defining two fixed orientations, one of which is in perpendicular to the horizontal plane of the backrest and the other is in the same direction of the horizontal plane of the backrest.

7. A therapeutic bed as defined in claim 1, wherein the drive means is comprised of a hydraulic cylinder.

8. A therapeutic bed for inversely suspending/standing a patient, comprising:

an intermediate and lower body support of the therapeutic bed for accommodating a lower body of the patient;

a backrest of the therapeutic bed rotatably connected to an end of the intermediate and lower body support for accommodating an upper body of the patient;

a plurality of frames provided under the intermediate and lower body support and the backrest and forming a bed angle adjustment mechanism;

a drive means for driving the bed angle adjustment mechanism formed of the frames to change the angles and positions of the intermediate and lower body support and backrest of the therapeutic bed;

shoulder pads provided at an end of the backrest for supporting shoulders of the patient; and a fastening means provided at an end of the intermediate and lower body support for fastening ankles of the patient.

9. A therapeutic bed as defined in claim 8, further comprising handrails provided on both sides of the intermediate and lower body support for being grasped by the patient and for preventing the patient from falling down from the bed.

10. A therapeutic bed as defined in claim 9, further comprising a remote controller provided adjacent to one of the handrails to control movements of the drive means for changing the angle and position of at least one of the intermediate and lower body support and the backrest through the bed angle adjustment mechanism.

11. A therapeutic bed as defined in claim 9, further comprising a safety belt on the intermediate and lower body support for fastening on the patient to promote safety when the therapeutic bed moves.

12. A therapeutic bed as defined in claim 8, wherein the shoulder pads on the backrest take two fixed orientations, one of which is in perpendicular to the horizontal plane of the backrest and the other is in the same direction of the horizontal plane of the backrest.

13. A therapeutic bed as defined in claim 8, wherein the shoulder pads on the backrest have two receptacles to receive a hook therein for defining two fixed orientations, one of which is in perpendicular to the horizontal plane of the backrest and the other is in the same direction of the horizontal plane of the backrest.

14. A therapeutic bed as defined in claim 8, wherein the drive means is comprised of a hydraulic cylinder.

15. A therapeutic bed as defined in claim 8, wherein the drive means is comprised of two hydraulic cylinders, one is used for driving the backrest, and the other is used for driving the intermediate and lower body support.

* * * * *